United States Patent [19]

Celmer et al.

[11] Patent Number: 4,496,546

[45] Date of Patent: Jan. 29, 1985

[54] ERYTHROMYCIN D AND ESTERS THEREOF

[75] Inventors: Walter D. Celmer, New London; Walter P. Cullen, East Lyme; Paul C. Watts, Mystic, all of Conn.; Riichiro Shibakawa, Handa, Japan; Junsuke Tone, Chita, Japan

[73] Assignee: Pfizer Inc., New York, N.Y.

[21] Appl. No.: 367,820

[22] Filed: Apr. 12, 1982

[51] Int. Cl.$^3$ .................... A61K 31/71; C07H 17/08
[52] U.S. Cl. ...................... 514/29; 536/7.2; 435/76; 435/253
[58] Field of Search ............ 536/7.2; 424/180

[56] References Cited
U.S. PATENT DOCUMENTS 3,884,903  5/1975  Jones et al. ................... 536/7.2
4,363,803  12/1982  Hauske ......................... 536/7.2

OTHER PUBLICATIONS

Majer et al., J. Am. Chem. Soc., 99, pp. 1620–1622, (1977).
Jones et al., J. Med. Chem., 15, pp. 631–634, (1972).
Martin et al., J. Med. Chem., 15, pp. 635–638, (1972).
Bartner et al., J. Chem. Soc., Perkin I, pp. 1600–1624, (1979).

*Primary Examiner*—Johnnie R. Brown
*Assistant Examiner*—Elli Peselev
*Attorney, Agent, or Firm*—Charles J. Knuth; Albert E. Frost; Robert K. Blackwood

[57] ABSTRACT

Fermentation of a culture of *Nocardia* sp. ATCC 39043 produces an antibiotic complex comprising erythromycin D, 3″,4″-di-O-acetylerythromcyin D, 3″-O-acetyl-4″-O-propionylerythromycin D and 4″-O-acetylerythromycin D. The components are separated and are each useful in vitro and in vivo as antibacterial agents. If erythromycin D is the desired product, the esters can be hydrolyzed prior to the separation of the erythromycin D.

12 Claims, No Drawings

ERYTHROMYCIN D AND ESTERS THEREOF

BACKGROUND OF THE INVENTION

A culture of the microorganism, designated Nocardia sp. ATCC 39043, directly produces erythromycin D by fermentation, together with esters comprising 4''-O-acetylerythromycin D, 3'',4''-di-O-acetylerythromycin D and 3''-O-acetyl-4''-O-propionylerythromycin D. The most valuable of these esters, the 3'',4''-diacetate, is the major component of the fermentation. If erythromycin D itself is the desired product, hydrolysis of the esters is optionally carried out in the broth prior to isolation of the erythromycin D.

Erythromycin D is one of a group of macrolide antibiotics having common structural characteristics as follows:

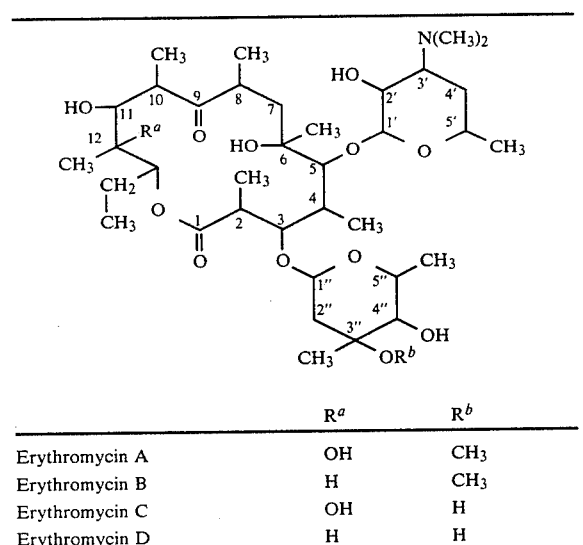

| | $R^a$ | $R^b$ |
|---|---|---|
| Erythromycin A | OH | CH₃ |
| Erythromycin B | H | CH₃ |
| Erythromycin C | OH | H |
| Erythromycin D | H | H |

Majer et al., J. Am. Chem. Soc., 99, pp. 1620-1622, (1977), isolated and identified erythromycin D as a trace component from an industrial erythromycin A purification side stream. The present invention provides a practical preparation of erythromycin D by direct fermentation.

Previously reported esters in the erythromycin series were made by chemical methods, not as fermentation products. These esters include the 2'-acetate, the 2'-propionate, the 4''-acetate and the 4''-propionate esters of both erythromycin A and erythromycin B. See Jones et al., J. Med. Chem. 15, pp. 631-634 (1972); Martin et al., J. Med. Chem., 15, pp. 635-637 (1972).

Structurally related esters have been previously reported as part of the megalomicin complex of antibiotics. Megalomicin A, having a third sugar moiety attached at C-6, otherwise corresponds in structure to erythromycin C. Other members of this series are esters of megalomicin A, as follows:

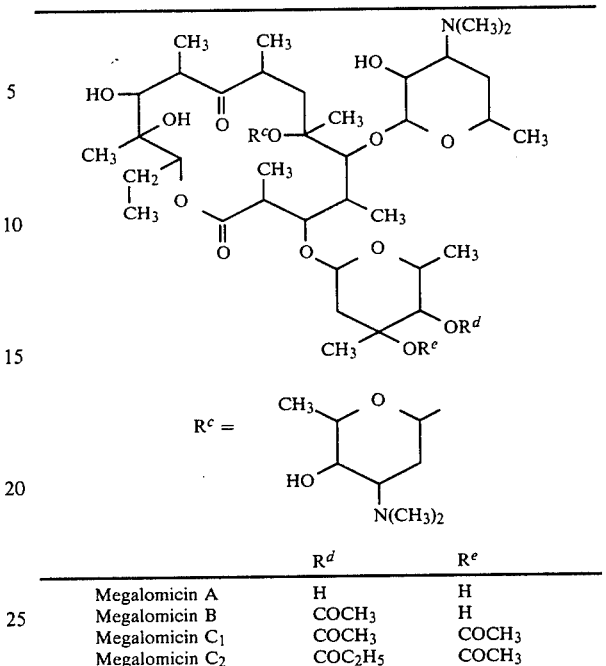

| | $R^d$ | $R^e$ |
|---|---|---|
| Megalomicin A | H | H |
| Megalomicin B | COCH₃ | H |
| Megalomicin C₁ | COCH₃ | COCH₃ |
| Megalomicin C₂ | COC₂H₅ | COCH₃ |

See Bartner et al., J. Chem. Soc., Perkin I, pp. 1600-1624 (1979).

SUMMARY OF THE INVENTION

A culture of Nocardia sp., ATCC 39043, when fermented under aerobic conditions in aqueous media, produces a complex of macrolide antibiotics comprising erythromycin D and novel mono- and diesters thereof, viz., the 3'',4''-diacetate, the 3''-acetate-4''-propionate and the 4''-acetate, as systematically named above according to the rules of carbohydrate nomenclature.

Although the culture of Nocardia sp. used in the present fermentation will generally be biologically pure (i.e., free of other contaminating microorganisms), this is not an essential feature of the present invention. The essential feature is that the culture is capable of producing the desired antibiotic complex.

As detailed below, the antibacterial activity of the present compounds is readily determined by methods well known in the art. This activity reflects their utility in the systemic or topical treatment of animal or human infections due to susceptible bacteria, in animal feeds as growth promotants, in the preservation of substances biodegradable by susceptible bacteria or as industrial disinfectants.

Preferred among the present esters is the 3'',4''-diacetate, because of its high degree of absorption via the oral route. Furthermore, this diacetate is the major component of the fermentation.

In addition to a culture of Nocardia sp. ATCC 39043 capable of producing the present antibiotic complex in recoverable quantities when fermented under aerobic conditions in an aqueous nutrient medium containing assimilable sources of carbon and nitrogen, and the freeze dried form thereof suitable for retention and storage of the microorganism, the present invention comprises: a process for producing said antibiotic complex by fermenting said Nocardia sp. until substantial antibiotic activity is obtained, and separating said antibiotic complex; said process further comprising separation of erythromycin D, its 4"-acetate, its 3",4"-diacetate or its 3"-acetate-4"-propionate from the antibiotic complex; said process further comprising hydrolysis of the esters in broth or after isolation of the antibiotic complex, and isolating erythromycin D therefrom; said erythromycin D esters per se, including pharmaceutically-acceptable acid addition salts thereof; and a method of treatment of a bacterial infection in a mammal with said erythromycin D esters.

Pharmaceutically-acceptable acid addition salts include, but are not limited to, those with hydrochloric acid, sulfuric acid, nitric acid, phosphoric acid, citric acid, maleic acid, succinic acid, benzenesulfonic acid, p-toluenesulfonic acid, 2-naphthalenesulfonic acid and methanesulfonic acid.

DETAILED DESCRIPTION OF THE INVENTION

The culture capable of producing the antibiotic complex of erythromycin D and its esters is designated Nocardia sp. and has been deposited in The American Type Culture Collection, Rockville, Md. as the type culture under their accession number ATCC 39043. Permanency of the deposit of this culture at The American Type Culture Collection at Rockville, Md. and ready accessibility thereto by the public are afforded throughout the effective life of the patent in the event the patent is granted. Access to the culture is available during pendency of the application under 37 CFR 1.14 and 35 USC 112. All restrictions on the availability to the public of the culture deposited will be irrevocably removed upon granting of the patent.

This novel culture was derived from a soil sample collected in Gose City, Nara Prefecture, Japan, and identified in the culture collection of Pfizer Inc. as N464-21. Its description and classification were provided by Dr. L. H. Huang. It is gram-positive, partially acid-fast, and has a white aerial mycelium and a not readily fragmented substrate mycelium whose color ranges from colorless, cream, pale yellowish to yellowish. The cell wall analyses of sugars, amino acids and mycolates further establish its assignment to the genus Nocardia.

An inoculum is prepared by plating from a freeze-dried lyophile into ATCC #172 broth and growing for 4 days at 28° C. on a shaker. It is then centrifuged for 20 minutes, washed three times with sterile distilled water and planted on media commonly used for identification of members of the Actinomycetales.

Incubation is made at 28° C. and the results may be read at varying times but most commonly is taken at 14 days. The colors are described in common terminology, but exact colors are determined by comparisons with color chips from the Color Harmony Manual, fourth edition. The methods of whole-cell and sugar analyses are those described in Becker et al., Appl. Microbiol. 12: 421–423, 1964; and in Lechevalier et al., J. Lab. Clin. Med. 71: 934–944, 1968. About 30 grams of autoclaved, wet mycelium were used for mycolate analyses, using the method described by Lechevalier et al. in J. Bacteriol. 105: 313–318, 1971.

The culture was identified as follows:

Yeast Extract-Malt Extract Agar (ISP #2 medium, Difco)—Growth good, dark yellowish (near 2ic), moderately raised, wrinkled, aerial mycelium white; reverse same as surface; no soluble pigment.

Oatmeal Agar (ISP #3 medium, Difco)—Growth poor to moderate, white, thin, smooth, aerial mycelium sparse, white; reverse colorless, no soluble pigment.

Inorganic Salts-Starch Agar (ISP #4 medium, Difco)—No growth.

Glycerol-Asparagine Agar (ISP #5 medium, Difco)—Growth good, yellowish (1½ga, 1½ia, 2ia), moderately raised, wrinkled, aerial mycelium white; reverse yellowish (1½ia); no soluble pigment.

Glucose-Asparagine Agar (Waksman, "The Actinomycetes", v. 2, medium #2, p. 328, 1961)—Growth good, white to cream (1½ca), slightly raised, smooth to slightly wrinkled, aerial mycelium white; reverse pale yellowish (1½ea); no soluble pigment.

Czapek-Sucrose Agar (Ibid., medium #1, p. 328)—Growth poor to moderate, white, thin, smooth, aerial mycelium sparse, observed only under the microscope; reverse colorless; no soluble pigment.

Glucose-Yeast Extract Agar (ibid., medium #29, p. 331)—Growth moderate, cream (1½ca), thin, smooth to slightly roughened, no aerial mycelium; reverse cream; no soluble pigment.

Emerson's Agar (ibid., medium #28, p. 331)—Growth moderate, cream (2ca), thin, smooth to slightly roughened, no aerial mycelium; reverse cream to pale yellowish (2ca, 2ea); no soluble pigment.

Nutrient Agar (ibid., medium #14, p. 330)—Growth moderate, cream (1½ca), thin to slightly raised, smooth, no aerial mycelium; reverse cream; no soluble pigment.

Bennett's Agar (ibid., medium #30, p. 331)—Growth good, white, cream to pale yellowish (2ca, 2ea), raised, wrinkled, aerial mycelium white; reverse pale yellowish (2ea); no soluble pigment.

Gordon and Smith's Tyrosine Agar (Gordon and Smith, J. Bact., 69: 147–150, 1955)—Growth moderate, cream (1½ca), thin, smooth, aerial mycelium sparse, observed only under the microscope; reverse colorless to cream; no soluble pigment.

Calcium Malate Agar (Waksman, Bact. Rev. 21, 1–29, 1957)—Growth moderate, cream to pale yellowish (1ca, between 1ca and 1ea), thin, smooth, with a few white dots, aerial mycelium white to cream; reverse pale yellowish (1ea); no soluble pigment.

Casein Agar (Gordon and Smith, ibid.)—Growth moderate, white, thin, smooth, aerial mycelium white; reverse colorless; no soluble pigment.

Gelatin Agar (Gordon and Mihm, J. Bact. 73, 15–27, 1957)—Growth moderate, white, thin, smooth, may be slightly wrinkled near the edge, aerial mycelium white; reverse colorless to cream (1½ca); no soluble pigment.

Starch Agar (ibid.)—Growth moderate, white, thin, smooth, or slightly wrinkled near the edge, aerial mycelium white; reverse cream (1½ca); no soluble pigment.

Potato Carrot Agar (Lechevalier, Lab. Clin. Med, 71, 934–944, 1968, but use only 30 g. potatoes, 2.5 g. carrots and 20 g. agar)—Growth moderate, white, thin, smooth, aerial mycelium white; reverse colorless; no soluble pigment.

Tap Water Agar (2%)—Growth scant to poor, white, thin, smooth, submerged, aerial mycelium sparse, observed only under microscope; reverse colorless; no soluble pigment.

Morphological Properties: The fragmentation study was made once every day up to 5 days on glucose-asparagine agar. Fragmentation of the mycelium occurred five days after inoculation. The following morphological observations were made on glucose-asparagine agar after 16-day inoculation; aerial mycelium white, flexuous, wavy or zig-zagged, 0.5-0.9 μm. in diam., may contain swellings and fragments; the swellings terminal, lateral or intercalary, single or contiguous, globose, oval to elliptical, 0.8-1.6 μm in diam., or 1.2-3×0.7-1.8 μm; the fragments 1.8-6 (or longer)×0-.7-0.9 μm, smooth as revealed by scanning electron microscopy; both the swellings and the fragments often contain refractive oil globules.

Biochemical Properties: Gram-positive; partially acid-fast; melanin production negative; production of hydrogen sulfide negative; nitrate reduction positive; gelatin liquefaction negative; hydrolysis of esculin, hippurate and starch (Gordon et al., Int. J. Syst. Bact., 24, 54-63, 1974) positive; decomposition of adenine, hypoxanthine, and xanthine (ibid.) positive; decomposition of calcium malate, casein, cellulose, tyrosine and urea (ibid.) negative; resistance to lysozyme (ibid.) positive; no growth in Jensen's (Proc. Linn, Soc. N.S.W. 55: 231-248, 1930) or Levine and Schoenlein's (A Compilation of Culture Media, medium #2511, 1930) broth; no coagulation and no peptonization on skim milk (Difco).

Utilization of organic acids (Gordon et al., loc. cit.): acetate, malate, propionate and pyruvate utilized; benzoate, citrate, dextrin, lactate, mucate, oxalate, phenol, succinate, and tartrate not utilized.

Acid production from carbohydrates (ibid.): Acid produced from fructose, galactose, glucose, glycerol, inositol, mannitol, mannose, raffinose, ribose, salicin, starch and sucrose; acid not produced from adonitol, arabinose, cellobiose, dulcitol, erythritol, lactose, maltose, melezitose, melibiose, rhamnose, sorbitol, sorbose, trehalose, xylose, and alpha-methyl-d-glycoside.

Carbohydrate utilization (ibid.): Arabinose, fructose, galactose, glucose, glycerol, inositol, maltose, mannitol, mannose, melezitose, raffinose, ribose, salicin, sorbitol, starch, sucrose, trehalose, and xylose utilized; cellobiose, sorbose, and alpha-methyl-d-glycoside doubtfully utilized; adonitol, dulcitol, erythritol, lactose, melibiose, and rhamnose not utilized.

Temperature Relation (ATCC medium #196 in "ATCC Culture Collection Catalog" 14th ed., p. 519, 1980): The culture shows good to excellent growth at 28° C., good growth at 21° C. and 37° C., and no growth at 10° C. and 45° C. It survives at 50° C. for 8 hours.

Cell Wall Analysis: The cell wall contains mesodiaminopimelic acid, arabinose, and galactose.

Mycolate Analysis: The cell wall contains nocardomycolates.

The morphological properties, the nocardomycolic acids, and a type IV cell wall (meso-diaminopimelic acid, arabinose, and galactose) indicate the placement of the present culture in the genus Nocardia. The culture is related to *Nocardia paraffinae* (Jensen) Waksman and Henrici and *N. otitidis-caviarum* Snijders in some morphological and biochemical properties. It differs from *N. paraffinae* in failure to produce acid from maltose, failure to utilize benzoate and succinate, and failure to hydrolyze urea. Five differences distinguish it from *N. otitidis-caviarum*: failure to produce acid from maltose and trehalose, inability to hydrolyze urea, no coagulation on milk, and no growth at 45° C.

To produce the antibiotic complex comprising erythromycin D and its esters (the 3″,4″-diacetate, the 3″-acetate-4″-propionate and the 4″-acetate), the present Nocardia sp. is fermented for three to thirteen days, suitably at 24°-36° C. under submerged conditions with agitation and aeration on media consisting of *carbohydrate sources* such as sugars, starches, glycerol; *organic nitrogen substances* such as soybean meal, casamino acids, yeast extract; *growth substances* such as grain solubles, fish meal, cotton seed meal; *mineral salts* containing trace elements such as iron, cobalt, copper, zinc, etc. and calcium carbonate or phosphates as buffering agents.

The inoculum required for the fermentation is prepared by scraping vegetative cells from slants or Roux bottles incubated with the Nocardia culture. A solid medium suitable for initial growth on slants and Roux bottles in ATCC medium #172:

|  | gms/liter |
|---|---|
| Glucose | 10 |
| Soluble Starch | 20 |
| Yeast Extract | 5 |
| NZ Amine A | 5 |
| Calcium Carbonate | 1 |
| Distilled Water to 1000 ml; pH to 7.0 with KOH | |
| Add Agar | 20 |

Vegetative cells from slants are used to inoculate either shake flasks or inoculum tanks; or alternately the inoculum tanks are inoculated from shake flasks. In shake flasks growth will generally have reached its maximum in 4 to 6 days whereas in the inoculum tanks growth will usually be at the most favorable period in 3 to 5 days after inoculation. A fermentor can be inoculated with vegetative broth from the inoculum flasks or tank under completely aseptic conditions and fermented for a period of 4 to 6 days. Aeration is maintained in the shake flask by agitation on a shaker or in tanks by forcing sterile air through a sparger at the rate of ½ to 2 volumes of air per volume of broth per minute. The speed of agitation (stirring) depends upon the type of agitator employed; a shake flask is usually run at 150 to 200 cycles per minute and a fermentor at 300 to 1700 revolutions per minute. Sterility is maintained at all times. The temperature is regulated between 26° C. and 34° C. Foaming during the fermentation can be controlled with sterile antifoam such as refined soybean oil, or other suitable antifoam agents in the makeup and as needed aseptically after inoculation.

Typical fermentation media (with code letter designations of Pfizer Inc.) are as follows:

|  | JD | JL | JLZ-M-1 |
|---|---|---|---|
| Cerelose | 10 g/l. | 10 | 2 |
| Corn starch | 5 | 10 | 10 |
| Corn steep liquor | 5 | — | — |
| Soy flour | — | 10 | 15 |
| Corn fermentable solubles | — | 5 | — |
| Casein | 5 | — | — |
| BYF 300 Yeast | — | — | 5 |
| NZ Amine Ytt | — | 5 | 10 |
| Sodium chloride | — | 2.5 | — |
| Calcium carbonate | 3 | — | 2 |
| Cobalt chloride | 0.002 | 0.01 | 0.01 |
| Potassium phosphate dibasic | — | — | 1 |
| Magnesium sulfate | — | — | 0.5 |
| Acetic acid | — | — | 1.05 (1 ml.) |
| pH | 7.2-7.3 | 7.1-7.2 | — |

|  | JLC-3 | JLC-3' | JLC-6 | JLC-6' |
|---|---|---|---|---|
| Glucose | 20 g/l. | 20 | 20 | 20 |

-continued

|  | JLC-3 | JLC-3' | JLC-6 | JLC-6' |
|---|---|---|---|---|
| NZ Amine-type A | — | 10 | — | 10 |
| Casamino acid | 10 | — | 10 | — |
| Blood meal | 10 | 10 | 10 | 10 |
| DL-Valine | — | — | 5 | 5 |
| DL-Leucine | 10 | 10 | — | — |
| NaCl | 4 | 4 | 4 | 4 |
| $CaCO_3$ | 4 | 4 | 4 | 4 |
| $MgCl_2.6H_2O$ | 5 | 5 | 5 | 5 |
| Isoamylalcohol | 0.82 (1 ml.) | 0.82 (1 ml.) | 0.82 (1 ml.) | 0.82 (1 ml.) |
| Phosphate buffer (M/50) | added | added | added | added |

The antibiotics can be recovered by extracting the whole broth at alkaline pH with a suitable water immiscible organic solvent such as chloroform, ethyl acetate or methylisobutyl ketone. The solvent is separated and back extracted into acid water. Unlike erythromycin A, erythromycin D and its esters are fairly stable at acid pH (2.5 to 5.0). The aqueous layer is separated, adjusted to pH 8.0–9.0 and re-extracted with the same or a different water immiscible organic solvent. The antibiotic complex is recovered by evaporation of the solvent and chromatography of the residue. The components of the antibiotic complex are separated by further chromatography.

The above-defined pharmaceutically-acceptable acid addition salts of the present invention are readily prepared by standard methods. For example, an equivalent of the acid is combined with the free amine form of the compound in an organic or aqueous organic solvent. The salt is isolated by concentration and/or the addition of a non-solvent. In some cases, the salt is isolated directly from a reaction mixture, without isolation of the free amine.

If erythromycin D is the desired end product, it is preferable to hydrolyze the esters at some stage in the process prior to isolation of the purified erythromycin D. This minimizes the processing and maximizes the yield of erythromycin D. Hydrolysis can be carried out on broth by simply making the broth weakly basic with a base such as saturated barium hydroxide or dilute sodium or potassium hydroxide or carbonate solution. Alternatively, hydrolysis is carried out on a crude concentrate, on the isolated antibiotic complex or on the isolated esters in an aqueous or alcoholic solvent employing a base as defined above.

Erythromycin D and the esters of the present invention exhibit in vitro activity against a medium spectrum of Gram-positive and Gram-negative bacteria. Table I summarizes the results of in vitro MIC (minimum inhibitory concentration) tests. For this standard test, each organism is inoculated into a series of tubes containing nutrient medium and serially diluted concentrations of the antibiotic. The MIC is the lowest concentration of antibiotic which prevents growth of the microorganism over the 24 hour incubation test period.

Erythromycin D and the esters of the present invention also exhibit in vivo activity against infections by sensitive bacteria, as summarized in Table II. In determining such activity, acute experimental infections are produced in mice by the intraperitoneal inoculation of the mice with a standardized culture of the test organism suspended in 5 percent hog gastric mucin. Infection severity is standardized so that the mice receive at least one $LD_{100}$ dose of the organism ($LD_{100}$: the minimum inoculum of organism required to consistently kill 100 percent of the infected, nontreated control mice). The test compound is orally administered at various dosage levels to groups of infected mice at ½, 4 and 24 hours post infection. At the end of the test, the activity of the mixture is assessed by counting the number of survivors among treated animals at a given dose. Activity is expressed as the percentage of animals which survive at a given dose, or calculated as a $PD_{50}$ (dose which protects 50% of the animals from infection).

TABLE I

In vitro Activity of Erythromycin D and Esters

| Microorganism[a] |  | MIC (mcg/ml) | | | |
|---|---|---|---|---|---|
|  |  | D[b] | DAA[c] | DAP[d] | DA[e] |
| Staph. aureus | 005 | 0.39 | 1.56 | 0.39 | 3.12 |
|  | 052 | 0.39 | 3.12 | 0.78 | 6.25 |
|  | 400 | 6.25 | 50 | 12.5 | f |
| Staph. epid. | 111 | 0.20 | 0.39 | 0.20 | 0.78 |
| Strep. faec. | 006 | 0.39 | 1.56 | 0.78 | 3.12 |
| Strep. pyog. | 203 | 0.025 | 0.10 | 0.05 | 0.20 |
| Strep. pneum. | 012 | 0.025 | 0.10 | 0.05 | 0.39 |
| E. Coli | 470 | 3.12 | 12.5 | 12.5 | 6.25 |
| Past. mult. | 001 | 6.25 | 25 | 12.5 | 25 |
| Neiss. Sicca | 000 | 6.25 | 25 | 12.5 | 25 |
| Hem. influ. | 036 | 50 | f | f | f |
|  | 012 | 25 | f | 50 | 50 |

[a]All compounds resulted in MIC greater than 50 with Staph. aureus 110; Staph. epid. 087 and 126; Strep. pyog. 054; E. coli 125, 129 and 266; Pseudomonas aerug. 104 and 663, K. pn. 009 and 031; K. oxy. 024, Serr. marc. 017; Ent. aerog. 040; Ent. cloac. 009; Prov. stua. 013; Prov. ret. 025; and Morg. morg. 001.
[b]Erythromycin D.
[c]3",4"-Diacetate.
[d]3"-Acetate-4"-propionate.
[e]4"-Acetate.
[f]MIC greater than 50.

TABLE II

In vivo Activity of Erythromycin D and Esters
Oral Dosage ½, 4 and 24 hours Post Infection

| Antibiotic | $PD_{50}$ (mg/kg) | |
|---|---|---|
|  | Staph aureus 005 | Strep pyogenes 203 |
| Erythromycin D | 57 | 15 |
| 4"-O—acetyl-erythromycin D | 139 | 40 |
| 3",4"-Di-O—acetyl-erythromycin D | 27 | 15 |
| Erythromycin A | 64 | 25 |

For the treatment of systemic infections in animals, including man, caused by suseptible microorganisms, the present compounds are dosed at a level of 2.5–100 mg/kg. per day, preferably 5–50 mg/kg./day, usually in divided doses. Variation in dosage will be made depending upon the individual and upon the susceptibility of the microorganism. These compounds are dosed orally or parenterally, the preferred route of administration being oral. The susceptibility of microorganisms isolated in the clinics is routinely tested in clinical laboratories by the well-known disc-plate method.

Preparation of optimal dosage forms will be by methods well known in the pharmacists art. For oral administration, the compounds are formulated alone or in combination with pharmaceutical carriers such as inert solid diluents, aqueous solutions or various non-toxic organic solvents in such dosage forms as gelatin capsules, tablets, powders, lozenges, syrups and the like. Such carriers include water, ethanol, benzyl alcohol; glycerin, propylene glycol, vegetable oils, lactose, starches, talc, gelatins, gums and other well known carriers. For parenteral administration, the compounds are dissolved or suspended in a pharmaceutically-acceptable carrier such as water, saline, sesame oil, and the like. Agents which improved the suspendability and dispersion qualities can also be added.

For the topical treatment of superficial infections in animals, including man, caused by susceptible microorganisms, the present compounds are formulated by methods well known in the pharmacist's art into lotions, ointments, creams, salves, gels, or the like at concentrations in the range 5–200 mg/cc. of the dosage form, preferably in the range 10–100 mg/cc. The dosage form is applied at the site of infection ad libitum, generally at least once a day.

When the antibacterial compounds of the present invention are used as preservatives of biodegradable materials, they are simply blended with the biodegradable material at a concentration which is at least sufficient to inhibit the growth of the bacteria causing biodegradation. Routine serial dilution techniques can be used to determine the concentrations necessary to achieve the desired purpose.

When the antibacterial compounds of the present invention are used as growth promotants in domestic food animals, they are provided by low levels (e.g. 10 g. to 100 g. of compounds per ton of feed). Blending of the compound with feed is usually accomplished in two stages, first in the preparation of a preblend (e.g. 10–100 g. of compound blended with 10–20 lb. of soybean mill run or the like), which is then blended with the feed at the time of milling.

When these compounds are used as industrial disinfectants, they are generally applied as dilute solutions to the surfaces which are to be disinfected.

The present invention is illustrated by the following examples. However, it should be understood that the invention is not limited to the specific details of these examples.

EXAMPLE 1

Fermentation in 2.5 Liter Pots

Twenty pots were prepared with JL medium, 2.5 liters of medium per pot. One milliliter antifoaming agent was added, and the vessels sealed and sterilized at 120° C. and 15 p.s.i. for 45 minutes. The pots were inoculated with one (2%) or two (4%) inoculum flasks of Nocardia sp. ATCC 39043, fermented for 3 to 6 days at 30° C. (stirred at 1700 revolutions per minute (RPM) and air sparged through the broth at one volume per volume per minute). When fermentation was complete (based on antibiotic disc assay versus *Micrococcus luteus* ATCC 9341 or *B. subtilis* ATCC 6633) the fermentors were stopped, adjusted to pH 8.0 to 9.0 with 50% sodium hydroxide and extracted with ⅓ volume of methylisobutyl ketone. The solvent layer was separated by centrifugation. After sparkling, the antibiotics were back extracted into acid water at pH 3.0, separated and the spent solvent discarded. The acid water was adjusted to pH 8.0 to 9.0, then extracted into ethyl acetate. The solvent was sparkled, dried with anhydrous sodium sulfate and concentrated. The concentrate weighed 2.5 grams.

The concentrate was dissolved in methanol and passed down a column of hydroxypropylated cross-linked dextran gel (Sephadex LH-20, available from Pharmacia Fine Chemicals), with methanol as eluant. The active cuts were combined and concentrated to a syrup, weight approximately 1.7 gms. This concentrate was ready for chromatographing on silica gel to isolate the purified antibiotic complex as detailed in Example 3.

The bioactivity of the broth, extracts and column cuts was followed by using a sensitive strain of *Bacillus subtilis* ATCC 6633, *Staphylococcus aureus* ATCC 6538, or *Micrococcus luteus* ATCC 9341. The individual components in the broth, extracts or column cuts were visualized by TLC using Analtech silica gel GF plates in the following systems, chloroform/methanol 9:1 or 3:1 v/v or chloroform/acetone/ammonium hydroxide 25:25:1 v/v/v and spraying the developed plates with vanillin reagent (5 grams vanillin in 100 ml. of ethanol and 50 ml. of 85% phosphoric acid). The plates were heated to 80° C. and the antibiotics were gray to blue/purple on a white background. The individual components were also visualized by overlaying the developed plate with the bacterial organism aforementioned in agar, adding tetrazolium and incubating the plates overnight at 37° C. The antibiotics appeared as clear zones against a reddish background.

EXAMPLE 2

Large-scale Nocardia sp. ATCC 39043 Fermentation

Scale-up in large fermentors (25 to 1000 gallons) were carried out by preparing large shake flasks containing 0.7 liters of JD or JL medium. The shake flasks inoculum was fermented 3 to 6 days at 28° C., and used to inoculate a 50, 250 or 1500 gallon fermentor containing 25, 100 or 1000 gallons of JL or JL2M-1 medium. The fermentors were harvested at 5 to 7 days.

A 1000 gallon fermentation was recovered by extracting the whole broth at pH 9.2 with 200 gallons of methylisobutyl ketone (MIBK). The MIBK extract was separated from the water layer, and back extracted into 25 gallons of acid water, pH 3.4. The acid water was adjusted to pH 9.5, and extracted with 10 gallons of MIBK. The MIBK layer was back extracted into 1 gallon of acid water at pH 2.5 and separated. The acid water was adjusted to 9.5, then extracted with 1 liter of ethyl acetate. The solvent layer was sparkled, then dried with anhydrous sodium sulfate. The ethyl acetate was concentrated to near dryness, yield 18 grams.

The concentrate in methanol was then passed down LH20 Sephadex in methanol and the active cuts combined and concentrated. The yield of concentrate was 12 g., ready for separation of purified antibiotic complex on silica gel.

EXAMPLE 3

Isolation of Purified Antibiotic Complex

A 50 gallon fermentation of Nocardia sp. ATCC 39043 was extracted with methylisobutyl ketone at a pH of approximately 9.0. Solvent removal left a dark oily residue which was carried through an acid-base work-up as described below. The oil was dissolved in 500 ml. of ethyl acetate (EtOAc) and 500 ml. of water added. The pH was adjusted to 9.0 with dilute NaOH with stirring and the aqueous layer discarded. The EtOAc layer was layered with 500 ml. of water and the pH adjusted with stirring to 3.0 with phosphoric acid. The EtOAc layer was discarded and the acidic aqueous portion layered with 500 ml. of EtOAc and the pH adjusted with stirring to 9.0 with dilute NaOH. The ethyl acetate layer was dried over sodium sulfate and stripped to yield 32.5 grams of red-brown oil. This oil was then chromatographed on 1200 grams of Sephadex LH-20 using methanol as an eluant to produce approximately 16 grams of viscous gum. Chromatography on silica gel utilizing 100% chloroform and increasing amounts of methanol (up to 5% methanol) gave two grams of antibiotic complex.

EXAMPLE 4

Pot Fermentation with In Broth Hydrolysis of Esters

It was observed by TLC analysis that extension of fermentation age increases the proportion of erythromycin D over esters in the broth, accompanied by a rise in pH. Alkaline hydrolysis conditions were then established for the hydrolysis of esters to erythromycin D in broth.

Fermentation was carried out in various media (3 l.) in 6 l. stirred pots at 26° C. for up to 13 days according to the procedure of Example 1. For hydrolysis, 0.5 ml. of whole broth was mixed with 0.5 ml. of saturated aqueous Ba(OH)$_2$. After 15 minutes shaking in a water bath at 30° C., the pH was adjusted to 6.0–8.0 by adding 0.2 ml. of 0.92N HCl. Intact and hydrolyzed broths were assayed for potency using an agar diffusion (plate) assay using Staph. aureus 005 with the 3″,4″-diacetate of erythromycin D as standard (i.e. activity is expressed as diacetate equivalents).

The following assays were determined:

| Medium | 7 Days Potency (mcg/ml) | | 8 Days Potency (mcg/ml) | |
|---|---|---|---|---|
| | Intact | Hydrolyzed | Intact | Hydrolyzed |
| JLC-3 | 21.7 | 87.2 | 17.6 | 88.4 |
| JLC-3′ | 18.9 | 56.3 | 28.9 | 111.0 |
| JLC-6 | 21.0 | 96.0 | 22.2 | 122.0 |
| JLC-6′ | 25.0 | 130.0 | 28.7 | 132.0 |

| Medium | 10 Days Potency (mcg/ml) | | 13 Days Potency (mcg/ml) | |
|---|---|---|---|---|
| | Intact | Hydrolyzed | Intact | Hydrolyzed |
| JLC-3 | 22.2 | 79.2 | 35.3 | 79.2 |
| JLC-3′ | 28.7 | 120.0 | 37.8 | 143.0 |
| JLC-6 | 22.2 | 97.5 | 32.9 | 97.5 |
| JLC-6′ | 26.9 | 143.0 | 40.7 | 143.0 |

After hydrolysis, the concentrated antibiotic complex, now enriched in erythromycin D, is isolated according to Example 1 and 2. Purified erythromycin D is isolated according to methods detailed in Examples below.

EXAMPLE 5

Erythromycin D by Hydrolysis of Isolated Antibiotic Complex

Antibiotic complex (16 g.) prepared according to the preceding Examples was treated with 20 ml. of conc. NH$_4$OH in methanol for 120 hours at room temperature. The reaction mixture was stripped to a foam and redissolved in ethyl acetate. Erythromycin D (5 l g.) was recovered according to the acid-base extraction work-up procedure of Example 3.

EXAMPLE 6

Isolation of Erythromycin D, 3″,4″-Di-O-acetylerythromycin D, 4″-O-Acetylerythromycin D and 3″-O-Acetyl-4″-O-propionylerythromycin D Antibiotic complex (49.05 g.), prepared according to the preceding Examples, was placed on a preparative chromatography column (Jobin-Yvon Chromatospec) packed with 1600 g. silica gel (230–400 mesh) made up in heptane. Fractions of 500 ml. were taken as the solvent was changed to chloroform and then chloroform containing increasing amounts of methanol (up to 20%). The fractions were monitored by TLC, utilizing 1:1 chloroform:methanol as eluant and vanillin spray as described in Example 1. The Rf values of the individual components and yields of crude products by evaporation of appropriately combined fractions were:

| | Rf | Yield of Crude |
|---|---|---|
| (1) 3″-acetate-4″-propionate | 0.69 | 9.86 g. |
| (2) 3″,4″-diacetate | 0.65 | 8.47 g. |
| (3) 4″-acetate | 0.47 | 24.3 g. |
| (4) erythromycin D | 0.35 | 3.0 g. |

Each of combined fractions (1), (2) and (4) were column chromatographed on 25×1000 mm. columns of silica gel using chloroform containing increasing methanol (up to 5%) to produce analytically pure samples as follows:

| | |
|---|---|
| (1) 3″-acetate-4″-propionate | 80 mg. |
| (2) 3″,4″-diacetate | 760 mg. |
| (4) erythromycin D | 1.0 g. |

Combined fraction (3) was rerun on the preparative column to yield 2.19 g. of analytical grade 4″-acetate.

The following physicochemical properties were noted on these products:

3″-O-Acetyl-4″-O-propionylerythromycin D: m.p. 122°–132° C.; no meaningful uv in methanol; ir (KBr) 3500, 2980, 2960, 1470, 1380, 1240, 1180, 1020, 1010, 755 cm$^{-1}$.

3″,4″-di-O-Acetylerythromycin D: m.p. 123°–130° C.; uv (MeOH) 282 nm (max); ir (KBr) 3490, 2980, 2960, 1740, 1460, 1380, 1230, 1180, 1050, 1010 cm$^{-1}$.

4″-O-Acetylerythromycin D: m.p. 124°–130° C.; no meaningful uv in methanol; ir (KBr) 3510, 2980, 2940, 1742, 1460, 1380, 1240, 1180, 1110, 1050, 1010 cm$^{-1}$.

Erythromycin D: identical with previously characterized erythromycin D.

EXAMPLE 7

Erythromycin D by Hydrolysis of 3″,4″-Di-O-acetylerythromycin D

3″,4″-Di-O-acetylerythromycin D (27 mg.) was stirred for 16 hours with 1.0 ml. of 0.1N methanolic KOH at room temperature. Evaporation to dryness gave a white solid which, on ethyl acetate-acid-base extraction work-up according to Example 3, gave erthyromycin D.

EXAMPLE 8

3″,4″-di-O-Acetylerythromycin D Hydrochloride

3″,4″-Di-O-acetylerythromycin D (250 mg.) is dissolved in 10 ml. of methanol and the solution cooled to 0°–5° C. One equivalent of dry hydrogen chloride (2% in methanol) is added dropwise with stirring at 0°–5° C. The title salt is recovered by evaporation of the solvent in vacuo.

We claim:

1. An ester of erythromycin D which is:
3″,4″-di-O-acetylerythromycin D;
3″-O-acetyl-4″-O-propionylerythromycin D, or
4″-O-acetylerythromycin D;
or a pharmaceutically-acceptable acid addition salt thereof.

2. The ester of claim 1 which is 3″,4″-di-O-acetylerythromycin D, or a pharmaceutically-acceptable acid addition salt thereof.

3. The ester of claim 1 which is 3″-O-acetyl-4″-O-propionylerythromycin D, or a pharmaceutically-acceptable acid addition salt thereof.

4. The ester of claim 1 which is 4″-O-acetylerythromycin D, or a pharmaceutically-acceptable salt thereof.

5. A pharmaceutical composition suitable for the treatment of a bacterial infection in a mammal which comprises an antibacterially effective amount of a compound of claim 1 in combination with an inert carrier.

6. A pharmaceutical composition suitable for the treatment of a bacterial infection in a mammal which comprises an antibacterially effective amount of the compound of claim 2 in combination with an inert carrier.

7. A pharmaceutical composition suitable for the treatment of a bacterial infection in a mammal which comprises an antibacterially effective amount of the compound of claim 3 in combination with an inert carrier.

8. A pharmaceutical composition suitable for the treatment of a bacterial infection in a mammal which comprises an antibacterially effective amount of the compound of claim 4 in combination with an inert carrier.

9. A method for treating a bacterial infection in a mammal which comprises administering to said mammal an antibacterially effective amount of a compound of claim 1.

10. A method for treating a bacterial infection in a mammal which comprises administering to said mammal an antibacterially effective amount of the compound of claim 2.

11. A method for treating a bacterial infection in a mammal which comprises administering to said mammal an antibacterially effective amount of the compound of claim 3.

12. A method for treating a bacterial infection in a mammal which comprises administering to said mammal an antibacterially effective amount of the compound of claim 4.

* * * * *